United States Patent
Hong et al.

(10) Patent No.: US 8,193,804 B2
(45) Date of Patent: Jun. 5, 2012

(54) DEVICE FOR MEASURING AC MAGNETIZATION OF MATERIALS

(76) Inventors: Rex Chin-Yih Hong, Taipei (TW);
Herng-Er Horng, Taipei (TW);
Hong-Chang Yang, Taipei (TW);
Shieh-Yueh Yang, Taipei (TW)

( * ) Notice: Subject to any disclaimer, the term of this patent is extended or adjusted under 35 U.S.C. 154(b) by 494 days.

(21) Appl. No.: 12/394,043

(22) Filed: Feb. 27, 2009

(65) Prior Publication Data

US 2009/0164161 A1     Jun. 25, 2009

Related U.S. Application Data

(63) Continuation-in-part of application No. 11/164,275, filed on Nov. 16, 2005, now Pat. No. 7,560,289.

(51) Int. Cl.
*G01N 27/74* (2006.01)
*G01N 15/06* (2006.01)
*G01R 33/12* (2006.01)

(52) U.S. Cl. ........................................... 324/204

(58) Field of Classification Search .............. 324/204; 73/53.07; 702/149

See application file for complete search history.

(56) References Cited

U.S. PATENT DOCUMENTS

| | | | | |
|---|---|---|---|---|
| 5,001,424 A | * | 3/1991 | Kellett et al. | 324/204 |
| 6,051,970 A | * | 4/2000 | Hutchings | 324/204 |
| 6,911,818 B2 | * | 6/2005 | Julius | 324/204 |
| 7,148,678 B1 | * | 12/2006 | Targosz | 324/204 |
| 2007/0111330 A1 | | 5/2007 | Hong et al. | |
| 2007/0155024 A1 | | 7/2007 | Miethe et al. | |

FOREIGN PATENT DOCUMENTS

EP  1262766  12/2002

OTHER PUBLICATIONS

"Extended Search Report of European Counterpart Application", issued on Jun. 29, 2010, p. 1-p. 8.
Hong Chin-Yih et al; "Wash-free immunomagnetic detection for serum through magnetic susceptibility reduction", Applied Physics Letters, AIP, American Institute of Physics, Melville, NY, US, vol. 90, No. 7, Feb. 13, 2007, pp. 074105-1 to 074105-3, 3pages.
Hans-Joachim Krause et al.; "Magnetic particle detection by frequency mixing for immunoassay applications", Journal of Magnetism and Magnetic Materials, Elsevier Science Publishers, Amsterdam, NL, vol. 311. No. 1, Mar. 15, 2007, pp. 436-444, 9pages.

* cited by examiner

*Primary Examiner* — Jay Patidar
(74) *Attorney, Agent, or Firm* — Jianq Chyun IP Office

(57) ABSTRACT

Disclosed is an apparatus for measuring ac magnetization at mixture frequency. The apparatus includes an ac generating unit for generating at least a first current with a frequency $f_1$ and a second current with a frequency $f_2$. The apparatus further includes a co-axial solenoid unit, driven by the first and second ac currents, to generate a first magnetic field and a second magnetic field. A pick-up solenoid is for disposing sample for detecting an ac magnetization of the sample and multiple frequency-component signals corresponding to various frequency combinations of $f_1$ and $f_2$ are output. The apparatus further includes a signal processing circuit for receiving the frequency-component signals, where the signal processing circuit obtains the ac magnetization of the sample at a target frequency of $(\gamma_T f_1 + \beta_T f_2)$, which $\gamma_T$ and $\beta_T$ are positive integers and the frequency $f_1$ and the frequency $f_2$ are two different frequencies.

7 Claims, 8 Drawing Sheets

US 8,193,804 B2

DEVICE FOR MEASURING AC MAGNETIZATION OF MATERIALS

CROSS-REFERENCE TO RELATED APPLICATION

This application is a continuation-in-part of U.S. application Ser. No. 11/164,275, filed on Nov. 16, 2005, now pending. The entirety of the above-mentioned patent application is hereby incorporated by reference herein and made a part of this specification.

BACKGROUND OF THE INVENTION

1. Field of Invention

The present invention is related to measuring magnetization of magnetic fluid. More particularly, the present invention relates to device for measuring ac magnetization of materials and method for detecting bio-molecules.

2. Description of Related Art

Magnetic fluid is a colloid solution having magnetic nanoparticles dispersed in solvent. The material of magnetic nanoparticles is usually ferromagnetic. Thus, each magnetic nanoparticle owns permanent magnetic moment. In order to disperse stably magnetic nanoparticles in solvent, magnetic nanoparticles are coated with surfactant. For example, hydrophilic organic material is used for surfactant to disperse magnetic nanoparticles into aqueous solution. With aid of surfactant and nano-scale size, magnetic nanoparticles can be dispersed individually in solvent. Due to thermal energy, individual magnetic nanoparticles experience Brownian motion. Although each magnetic nanoparticle is ferromagnetic, i.e. exhibiting permanent magnetic moment, the directions of magnetic moments of magnetic nanoparticles are isotropic in liquid under zero magnetic field, so that the resultant magnetic moment of magnetic nanoparticles in liquid is zero under zero magnetic field. However, as a magnetic field is applied to magnetic fluid, magnetic moment of each magnetic nanoparticle tends to be aligned with the direction of the applied magnetic field. The theoretical analysis for the resultant magnetic moment (hereafter referred as to magnetization) M of magnetic fluid under an applied magnetic field H at temperature T can be expressed as Langevin function $$M(\xi) = M_o(\coth\xi - 1/\xi). \quad (1)$$

In Eq. (1), $M_o$, in which $M_o = Nm$, N is the total numbers of magnetic nanoparticles and m is the averaged magnetic moment of a magnetic particle, denotes the saturated magnetization, and $\xi$ can be written as $$\xi = \mu_o m H / k_B T, \quad (2)$$

where H is the applied magnetic field, $k_B$ is Boltzmann constant, $\mu_o$ is permeability of free space, and T represents the measurement temperature.

According to Eq. (1) and Eq. (2), at a given temperature T, the magnetization M of magnetic fluid increases monotonously with the increasing strength H of magnetic field, and then reaches to a saturated value under high H's. This saturated magnetization is $M_o$ in Eq. (1). When the applied magnetic field H is removed, i.e. H=0, the magnetization of magnetic fluid vanishes. The reversely zero magnetization of magnetic fluid as quenching an applied magnetic field is contributed by the directional randomization of magnetic moment of individual magnetic nanoparticles undergoing Brownian motion in liquid. This feature is so-called superparamagnetism.

In case of weak magnetic field being in several Gauss at room temperature (T about 300 K), $\xi$ is around $10^{-3}$ to $10^{-2}$.

Thus, the M in Eq. (1) can be expanded around $\xi$ being zero via Taylor expansion and is written as $$M(\xi \to 0) = M(0) + M^{(1)}(0)\cdot\xi + M^{(2)}(0)\cdot\xi^2 + M^{(3)}(0)\cdot\xi^3 + M^{(4)}(0)\cdot\xi^4 + M^{(5)}(0)\cdot\xi^5 + \ldots, \quad (3)$$

where $M^{(n)}$ denotes the $n^{th}$ derivation of M with respect to $\xi$ at $\xi=0$. One can find that the even-$n^{th}$-derivation terms on the right-hand side of Eq. (3) become zero, and $M^{(1)}=0.32$, $M^{(3)}=-0.12$. Eq. (3) can be expressed as $$M(\xi \to 0) = 0.32 M_o \mu_o m H / k_B T - 0.12 M_o (\mu_o m H / k_B T)^3 + O^5(\mu_o m H / k_B T) + \ldots \quad (4)$$

The fifth order of $O^5$ on the right-hand side in Eq. (4) denotes the term of power 5 of $\mu_o m H / k_B T$. If the applied magnetic field is generated by alternative-current (ac) and shows a frequency $f_o$, it can be found that the M exhibits non-zero components at frequencies of $\alpha f_o$, where $\alpha$ is positive odd integers. Consequently, magnetic fluid shows magnetization having frequencies of not only $f_o$ but also $\alpha f_o$ under a weak ac magnetic field with frequency $f_o$.

In Eq. (1) or (4), $M_o$ is proportional to the total numbers N of individual magnetic nanoparticles showing response to the applied ac magnetic field. Thus, in a given volume of magnetic fluid and under a fixed weak ac magnetic field having frequency $f_o$, the amplitude of $\alpha f_o$-component of the magnetization M spectrum decreases when the total numbers N of individual magnetic nanoparticles is reduced. The reduction in the total numbers N of individual magnetic nanoparticles showing a response to the applied ac magnetic field can be achieved by making magnetic nanoparticles clustered or larger through certain reactions in liquid. For example, the certain reactions can be the association between bio-probes and bio-targets in liquid. In such case, bio-probes are coated onto individual magnetic nanoparticles via the binding to the surfactant. Thus, magnetic nanoparticles become bio-functional and are able to bind with conjugated bio-targets.

For instance, the antibody acts as bio-probes and is coated onto individual magnetic nanoparticles in liquid. These bio-functionalized magnetic nanoparticles can bind with conjugated antigens. Due to the association between antigens and antibodies on individual magnetic nanoparticles, magnetic nanoparticles become clustered or larger. Hence, the total number N of individual magnetic nanoparticles in response to an applied ac magnetic field at certain fixed frequency is definitely reduced. So, it can be deduced that the amplitude of $\alpha f_o$-component of the magnetization M of bio-functionalized magnetic fluid decreases when magnetic nanoparticles bind with bio-targets. Furthermore, the decreasing in the amplitude is enhanced when more individual magnetic nanoparticles bind with bio-targets. Hence, the amount of bio-targets can be determined by measuring the reduction in the $\alpha f_o$-component of the magnetization M of bio-functionalized magnetic fluid. This is the fundamental mechanism for such bio-assay technology as immunomagnetic reduction (IMR).

In order to measure the ac magnetization of the sample, several conventional apparatus have been proposed. FIG. 1 schematically shows the conventional architecture to measure the magnetization of magnetic fluid under an ac magnetic field. An excitation solenoid 102 is driven by an ac current generator 100 at frequency $f_o$, so as to generate the ac magnetic field. A pick-up solenoid 104 is co-axially located inside the excitation solenoid 102. The pick-up solenoid 104 is referred as to magnetometer type. The magnetic fluid 108 is disposed inside the pick-up solenoid 104. The coil 106 is formed by the solenoids 102 and 104. The ac current generator 100 applies ac current at the frequency $f_o$ to the solenoid 102 of coil 106. Due to varying magnetic field, the pick-up solenoid 104 of coil 106 is induced ac voltage for output. However, the output of the ac voltage is relating to the magnetic fluid 108. As the ac magnetic field of frequency $f_o$ is applied, the magnetic fluid 108 is induced to generate ac magnetizations of various frequencies $\alpha f_o$, $\alpha=1, 3, 5, \ldots n$. The ac magnetizations are detected with the pick-up solenoid 104 of coil 106, which converts the signals from magnetization to voltage. Thus, ac voltages of frequencies $\alpha f_o$ are output from the pick-up solenoid 104 of coil 106 to an electronic circuit 110. The electronic circuit 110 processes the voltage signals, with respect to various frequency components, to obtain the quantity at the component with the target frequency $\alpha_T f_o$.

However, the measurement architecture shown in FIG. 1 has disadvantages. Firstly, in addition to the magnetizations generated by magnetic fluid, the ambient signals can be detected by the pick-up solenoid. Secondly, the ac magnetic field (at $f_o$) generated with the excitation solenoid 102 is also probed. Thus, the induced voltage of $f_o$ at the output of the pick-up solenoid 104 is much stronger than those at other frequencies. For the electronic circuit 110, it usually has amplifying units to amplify the voltage signal at $\alpha_T f_o$ for achieving high detection sensitivity. The amplifying units are operation amplifiers, having high-level limitation for the input voltages. The operation amplifiers can not properly work when input voltage is too high. When the input voltage at $\alpha_T f_o$ is amplified, the input voltage at $f_o$ is also amplified. With the high-level limitation of operation amplifiers, there is a limitation to amplify the voltage signal at $\alpha_T f_o$ in order to keep the total input voltages below the high-level limitation of operation amplifiers. Thirdly, due to the sub-harmonic effect of electronic circuit, there exit output voltages at frequencies of $f_o$, $2f_o$, $3f_o$, $4f_o$, $5f_o$, $\ldots$ etc., when there is input voltage at $f_o$ from the output of the pick-up solenoid 104. These negative factors cause that the resultant output voltage of $\alpha_T f_o$ from the electronic circuit is attributed to the ambient signals, the excitation field, and sub-harmonic signals of electronic circuit. Therefore, the final output voltage at $\alpha_T f_o$ is not reliable, or even false.

To overcome the disadvantages in FIG. 1, another conventional design to measure the induced ac magnetization of magnetic fluid is proposed. FIG. 2 schematically shows the conventional architecture to measure the magnetization of magnetic fluid under an ac magnetic field. In FIG. 2, the pick-up solenoid 120 includes two sections: upper section and lower section. The coils in these two sections are wired in opposite direction and connected in series. The magnetic fluid 108 is disposed at one of the two sections, such as the upper section. Thus, ambient signals can be simultaneously sensed by these two sections. Voltages can be induced from out-leads of these two sections, and are cancelled with each other. Besides, by well aligning the position of the pick-up solenoid 120 inside the excitation solenoid 102, the induced voltage at $f_o$ by the ac magnetic field at $f_o$ generated by the excitation solenoid 102 are cancelled for the gradiometer-type pick-up solenoid 120. In practical cases, it is impossible to completely cancel the induced voltage at $f_o$ by aligning the pick-up solenoid 120 inside the excitation solenoid 102. But, the input voltage at $f_o$ to the electronic circuit can be greatly reduced for the measurement architecture in FIG. 2 as compared to that in FIG. 1. This means that the amplification in the electronic circuit can be significantly increased when using gradiometer-type pick-up solenoid. However, the existence of input voltage of $f_o$ also generates the sub-harmonic signals to the output as mentioned before. Thus, the signals from the sample at the target frequency $\alpha_T f_o$ usually have unwanted components.

In conclusion, the conventional designs can measure the ac magnetization of magnetic fluid. However, the target frequency is limited to $\alpha_T f_o$, multiple of base frequency $f_o$, resulting in unreliable output voltage at $\alpha_T f_o$ and their applications are limited.

SUMMARY OF THE INVENTION

In an aspect, the invention provides a method to quantitatively measure an amount of bio-molecules in a sample. The method includes providing a solution having magnetic nanoparticles; coating bioprobe molecules to surfaces of the magnetic nanoparticles in the solution; measuring a first alternating current (ac) magnetization of the solution at a mixture frequency $(\gamma f_1 + \beta f_2)$, wherein $\gamma$ or $\beta$ is independently an integer larger than zero; adding a sample containing the bio-molecules to be detected to the solution, so that the biomolecules in the sample conjugate with the bioprobe molecules coated on the nanoparticles; and measuring a second ac magnetization of the solution at the mixture frequency $(\gamma f_1 + \beta f_2)$ after adding the sample and incubation, so as to obtain an ac magnetization reduction at the mixture frequency $(\gamma f_1 + \beta f_2)$ between the first and the second magnetization to determine the amount of the bio-molecules.

In an aspect, the present invention also provides an apparatus to measure ac magnetization at mixture frequency. The apparatus includes an ac generating unit to generate at least a first ac current with a frequency $f_1$ and a second ac current with a frequency $f_2$. A co-axial solenoid unit is driven by the first ac current and the second ac current to generate a first magnetic field and a second magnetic field. A gradiometer-type pick-up solenoid is disposed within the co-axial solenoid unit, wherein a sample is disposed in the pick-up solenoid for detection an ac magnetization of the sample. Multiple frequency-component signals corresponding to various frequency combinations of $f_1$ and $f_2$ are output. A signal processing circuit receives the signals containing various frequency components, wherein the signal processing circuit processes the signals and obtains the ac magnetization of the sample at a target frequency of $(\gamma_T f_1 + \beta_T f_2)$. $\gamma_T$ and $\beta_T$ are positive integers and the frequency $f_1$ and the frequency $f_2$ are two different frequencies generated by the first and the second ac currents, respectively.

In an aspect, the present invention also provides a method to establish a relationship between an ac magnetization reduction and a bio-molecular concentration, wherein the ac magnetization reduction is a difference of ac magnetic susceptibilities in measured sample before and after the bio-molecules with known concentration are added into the measured sample. The method includes preparing a plurality of samples, wherein each of the samples include a solution having magnetic nanoparticles with coated bioprobe molecules thereon and bio-molecules with known concentration in the solution, wherein each sample has a different bio-molecular concentration. An ac magnetization reduction for each of the samples is measured. Data of the ac magnetization reductions are fitted by a Sigmoid function, such as logistic function, Equation (5) of:

$$IMR\ (\%) = \frac{A - B}{1 + \left(\frac{\phi}{\phi_o}\right)^p} + B, \qquad (5)$$

where IMR is the ac magnetization reduction in percentage, $\phi$ is the bio-molecular concentration in each sample, and A, B, $\phi_o$, and $\rho$ are fitting parameters to be fitted out to obtain a fitted curve. An ac magnetization reduction (IMR) for a to-be-measured sample is measured and a target bio-molecular concentration is obtained by using the fitted curve of the Eq. (5).

In an aspect, the present invention provides a method to observe reaction between magnetic nanoparticles and bio-molecule in a sample. The method comprises providing a solution having magnetic nanoparticles; coating bioprobe molecules to surfaces of the magnetic nanoparticles in the solution; adding a sample containing the bio-molecules to be detected to the solution for an incubation time; and measuring an alternating current (ac) magnetization of the solution at a mixture frequency ($\gamma f_1 + \beta f_2$) as function of time, wherein $\gamma$ and $\beta$ are independently integers larger than zero, $f_1$ and $f_2$ are two different frequencies. The ac magnetization is stable in an initial state and a reaction-completion state, but has a difference between the initial state and the reaction-completion state.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

In the invention, a method and an apparatus to measure ac magnetization at mixture frequency are proposed. In addition various applications haven been provided. Several embodiments are provided to depict the present invention. However, the present invention is not limited to the provided embodiments.

In considering the conventional design to measure the ac magnetization, to further reduce the effect from the excitation field and sub-harmonic signals of electronic circuit to the final output voltage at frequency of $\alpha_T f_o$, the present invention propose to use a mixed-frequency excitation technology and the compensation mechanism in the electronic circuit.

Figure 3:
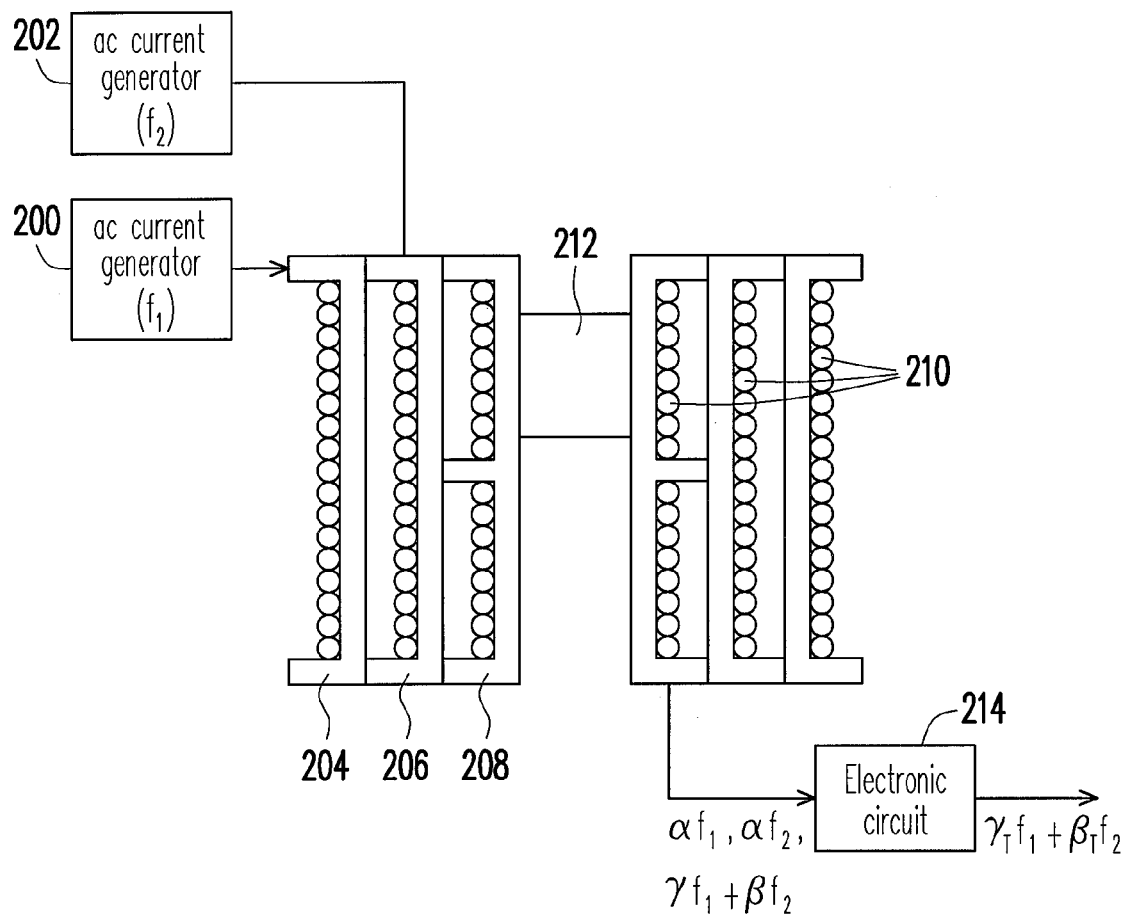
FIG. 3 schematically shows an architecture to measure the magnetization of magnetic fluid under an ac magnetic field, according to an embodiment of the present invention.

For mixed-frequency excitation, there is more than one frequency used for the applied magnetic field. In fact, at-least two magnetic fields having two different frequencies are applied simultaneously. For example, FIG. 3 schematically shows an architecture to measure the magnetization of magnetic fluid under an ac magnetic field, according to an embodiment of the present invention. In FIG. 3, the example producing the mixed-frequency excitation from two frequencies is illustrated. In this situation, there are two excitation solenoids 204, 206 aligned co-axially. The two excitation solenoids 204, 206 are respectively driven by ac current generators 200, 202 as a driving unit. The two ac current generators 200, 202 provide currents having different frequencies $f_1$ and $f_2$ separately to these two excitation solenoids 204, 206. Thus, H in Eq. (4) can be replaced with $H_1 + H_2$, where $H_1 = H_{1o} \cos(2\pi f_1 t)$ and $H_2 = H_{2o} \cos(2\pi f_2 t)$ with $f_1 \neq f_2$. Eq. (4) turns to be $$M(\xi \to 0) = 0.32 M_o \mu_o m(H_1+H_2)/k_B T - 0.12 M_o (\mu_o m/k_B T)^3 (H_1+H_2)^3 + (H_1+H_2)^5 O^5(\mu_o m/k_B T) + \ldots \quad (6)$$

Figure 1:
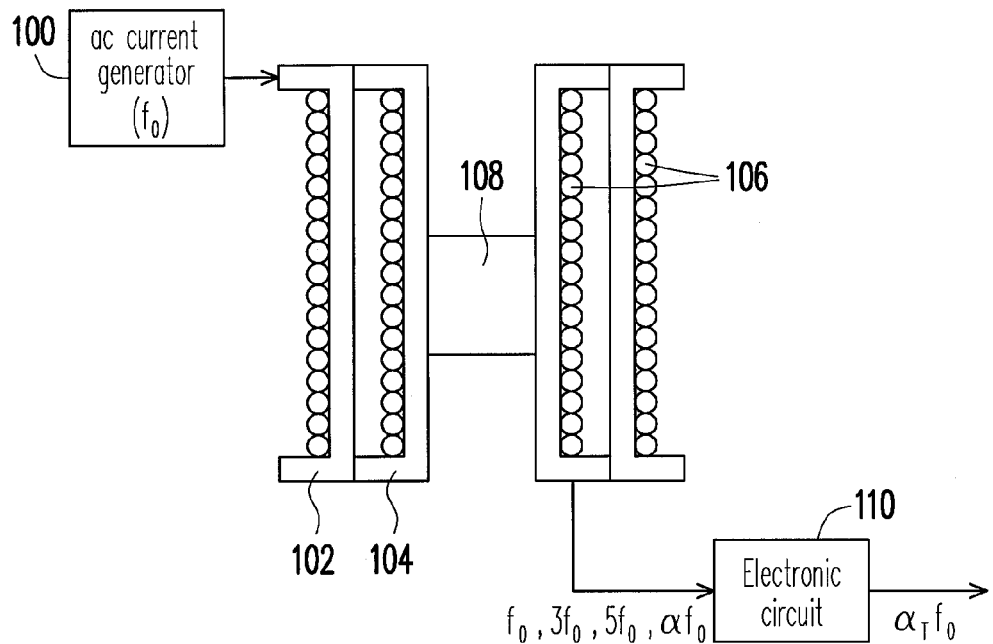
FIG. 1 schematically shows the conventional architecture to measure the magnetization of magnetic fluid under an ac magnetic field.
Figure 2:
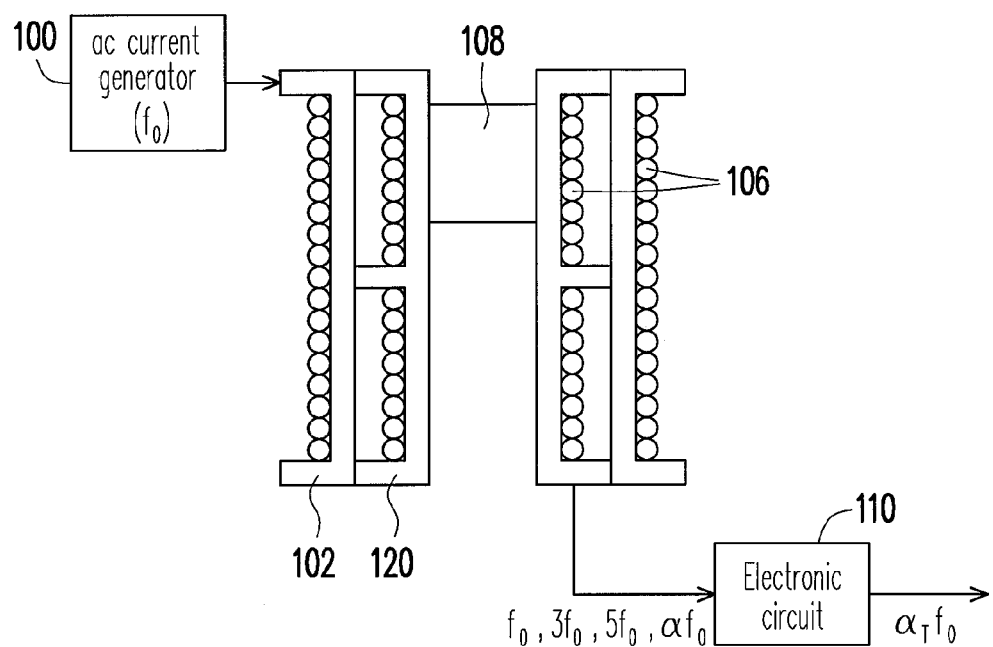
FIG. 2 schematically shows the conventional architecture to measure the magnetization of magnetic fluid under an ac magnetic field.

Eq. (6) reveals the fact that M is a combination of components having frequencies $\alpha f_1$, $\alpha f_2$, and $\gamma f_1 + \beta f_2$, where $\alpha$ is positive odd integers, and $\beta$ and $\gamma$ are non-zero integers. The pick-up solenoid 208 and the magnetic fluid 212 can be like the pick-up solenoid 104 and the magnetic fluid 108 in FIG. 1, for example. The coil 210 can be formed by solenoids 204, 206, and 208. It is clear that, in addition to the odd sub-harmonic frequencies of $f_1$ and $f_2$, the components having such frequencies as the linear combinations of $f_1$ and $f_2$ can be relating to the magnetization of magnetic fluid under the mixed-frequency excitation. If the base frequencies $f_1$ and $f_2$, are linear independent, the mixed-frequency components of the output signal from coil 210 are not be disturbed with the sub-harmonic effect in the electronic circuit 214 when these components are amplified with electronic circuit 214. Furthermore, by suitably selecting $f_1$ and $f_2$, the target frequency $\gamma_T f_1 + \beta_T f_2$ can be far away from those popularly used in telecommunication, city electric power system, etc. Thus, the contribution from ambience can be prevented to the component of $\gamma_T f_1 + \beta_T f_2$ for the magnetization of magnetic fluid under mixed-frequency excitation.

Usually, the amplitudes of the components of $\gamma f_1 + \beta f_2$ are much weaker then those of $\alpha f_1$ and $\alpha f_2$, $\alpha = 1, 2, 3, \ldots n$. So, the electronic circuit 214 needs to be designed to amplify the signals of components of $\gamma f_1 + \beta f_2$. However, as mentioned above, the sub-harmonic components (i.e. $\alpha f_1$ and $\alpha f_2$) lead to a bad performance in terms of amplification for the electronic circuit because of the high-level limitation of input signals to operation amplifiers in the electronic circuit 214. Hence, a compensation mechanism in the electronic circuit 214 is included to cancel the components of $\alpha f_1$ and $\alpha f_2$.

Figure 4:
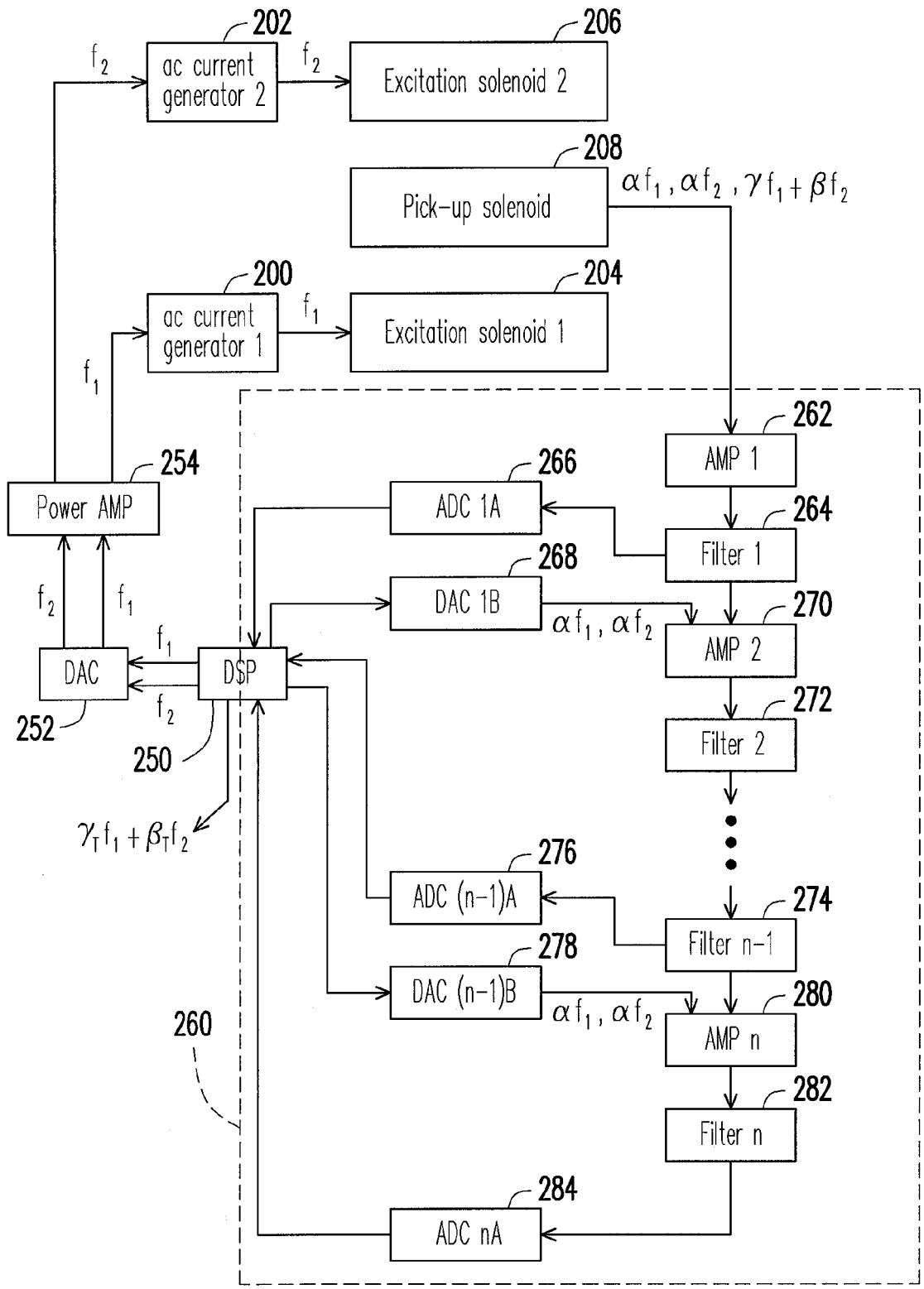
FIG. 4 schematically shows a circuit block diagram for measuring the magnetization of magnetic fluid, according to an embodiment of the present invention.

The block diagram of the electronic circuit designed here is shown in FIG. 4. Actually, the electronic circuit in FIG. 4 also includes the circuit for triggering ac current generators. The triggering signals having frequencies $f_1$ and $f_2$ respectively are generated with DSP, which signals are digital type and are converted to analog type through digital-to-analog converter (DAC) 252. The analog triggering signals $f_1$ and $f_2$ make ac current generators 200 and 202 to provide an ac current having frequency $f_1$ to excitation solenoid 1 204 and an ac current having frequency $f_2$ to excitation solenoid 2 206 via a power amplifier 254. The output signals from the gradiometer-type pick-up solenoid 208 are composed of frequencies of $\alpha f_1$, $\alpha f_2$, and $\gamma f_1 + \beta f_2$. All of these components are processed with the filtering/amplifying/compensating in the electronic circuit 214 to produce the target component at the mixed frequency $\gamma_T f_1 + \beta_T f_2$, $\gamma_T$ and $\beta_T$ are positive integers. Generally, different choice to the $\gamma_T$ and $\beta_T$ to obtain the mixed frequency may have different strength of signal being extracted out. The mixed frequency $\gamma_T f_1 + \beta_T f_2$ is a general condition and the quantities of $\gamma_T$ and $\beta_T$ are the design choices.

FIG. 4 schematically shows a circuit block diagram for measuring the magnetization of magnetic fluid, according to an embodiment of the present invention. In FIG. 4, the apparatus in FIG. 3 can be shown in electronic block diagram. The electronic circuit 214 in FIG. 3 includes the circuit 260, which includes a digital signal processing (DSP) unit 250, amplifiers 262, 270, 280, filters 264, 272, 274, 282, ADC's 266, 276, 284 and digital-to-analog converters (DAC's) 268, 278, form at least one stage to perform functions of filtering, amplifying, and compensation. In the example, n stages of signal processing are performed. In practical, n can be from 2 to five hundreds. Each filtering/amplifying/compensating part has the amplification factor from 1 to 1000 where 1 means no amplifier being used. For each unit, there is an amplifier and a bandpass filter with a center frequency at the target frequency.

The DSP unit 250 provides the harmonic frequencies of $f_1$ and $f_2$ as the base frequencies per design choice. The frequencies of $f_1$ and $f_2$ is converted into analog signal by the DAC 252 to inform the power amplifier 254 to control the ac current generators 200 and 202 for producing ac currents. As a result, the two excitation solenoids 204 and 206 are driven by the ac currents with different base frequencies of $f_1$ and $f_2$. The pick-up solenoid 208 with the magnetic fluid induces the signal spectrum with various resonant components at frequency of $\alpha f_1$, $\alpha f_2$, and $\gamma f_1 + \beta f_2$, $\alpha$, $\gamma$ and $\beta$ are positive integers, in which one of the components of $\gamma f_1 + \beta f_2$ is to be extracted out and amplified as the target frequency $\gamma_T f_1 + \beta_T f_2$.

The signals of components of $\alpha f_1$, $\alpha f_2$, and $\gamma f_1 + \beta f_2$ from the pick-up solenoid 208 are input to the 1$^{st}$ stage amplifier (AMP 1) 262. All of these components are amplified. However, the filter 1 264 with a central filtering frequency around the target frequency $\gamma_T f_1 + \beta_T f_2$ filters the other signal components. The 1$^{st}$ ADC 1A 266 converts analog signal into digital signal, which is input to the DSP 250 for finding amplitudes and phases of $\alpha f_1$ and $\alpha f_2$, especially $\alpha f_1$ and $\alpha f_2$ near the central frequency, $\beta_T f_1 + \beta_T f_2$. To compensate (or offset) the components of $\alpha f_1$ and $\alpha f_2$, the DSP unit 250 generates out-of-phase signals of $\alpha f_1$ and $\alpha f_2$ to cancel the components of $\alpha f_1$ and $\alpha f_2$ of amplified signals via a digital-to-analog converter DAC 1B 268. The 1$^{st}$-stage output signal and the out-of-phase signals of $\alpha f_1$ and $\alpha f_2$ of the DAC 1B 268 are output to the 2$^{nd}$-stage amplifier 270, in which the out-of-phase signals can be, for example, an invert phase so as to suppress the other signal component other than the target signal component with the frequency of $\gamma_T f_1 + \beta_T f_2$. Thus, the relative amplitude of $\gamma_T f_1 + \beta_T f_2$ with respect to other components increases. As a result, the amplitudes of $\alpha f_1$ and $\alpha f_2$ are not significantly amplified, and may even be reduced due to the compensation process. Moreover, the sub-harmonic effect of electronic circuit is also suppressed. Hence, it is possible to keep the total intensity of the output signal from the 1$^{st}$ unit below the high-level limitation of operation amplifiers in the 2$^{nd}$-stage amplifier 270. By using cascading filtering/amplifying/compensating units, the component of target frequency $\gamma_T f_1 + \beta_T f_2$ can be greatly amplified. The final output signal of all components of $\alpha f_1$, $\alpha f_2$, and $\gamma f_1 + \beta f_2$ is led to DSP via ADC nA 284. The amplitude of the target component at $\gamma_T f_1 + \beta_T f_2$ is analyzed and output from DSP unit 250.

An example to show the feasibility of the mixed-frequency excitation and filtering/amplifying/compensating electronic circuit is given. The sample to be detected is water-based dextran coated $Fe_3O_4$ magnetic fluid in this example, as to be described in FIG. 7. In addition to $Fe_3O_4$, the other materials, such as $MnFe_2O_4$, $CoFe_2O_4$, $Fe_2O_3$, ..., and so on, can also be used for magnetic nanoparticles. Other hydrophilic material such as protein A, protein G, etc. can be used to replace dextran coated onto the surface of magnetic nanoparticles. The mean diameter of magnetic nanoparticles in magnetic fluid is 56 nm for this example. It should be noted that the mean diameter of magnetic nanoparticles are not limited to 56 nm. General speaking, the mean diameter of magnetic nanoparticles can range from 5 nm to 500 nm. The frequencies of $f_1$ and $f_2$ can vary from 10 Hz to $10^6$ Hz, for example. The output amplitude of target component at $\gamma_T f_1 + \beta_T f_2$ is measured by using the filtering/amplifying/compensating electronic circuit in FIG. 4 for magnetic fluids of various concentrations from zero to 0.3 emu/g, or even to higher concentrations.

Figure 5:
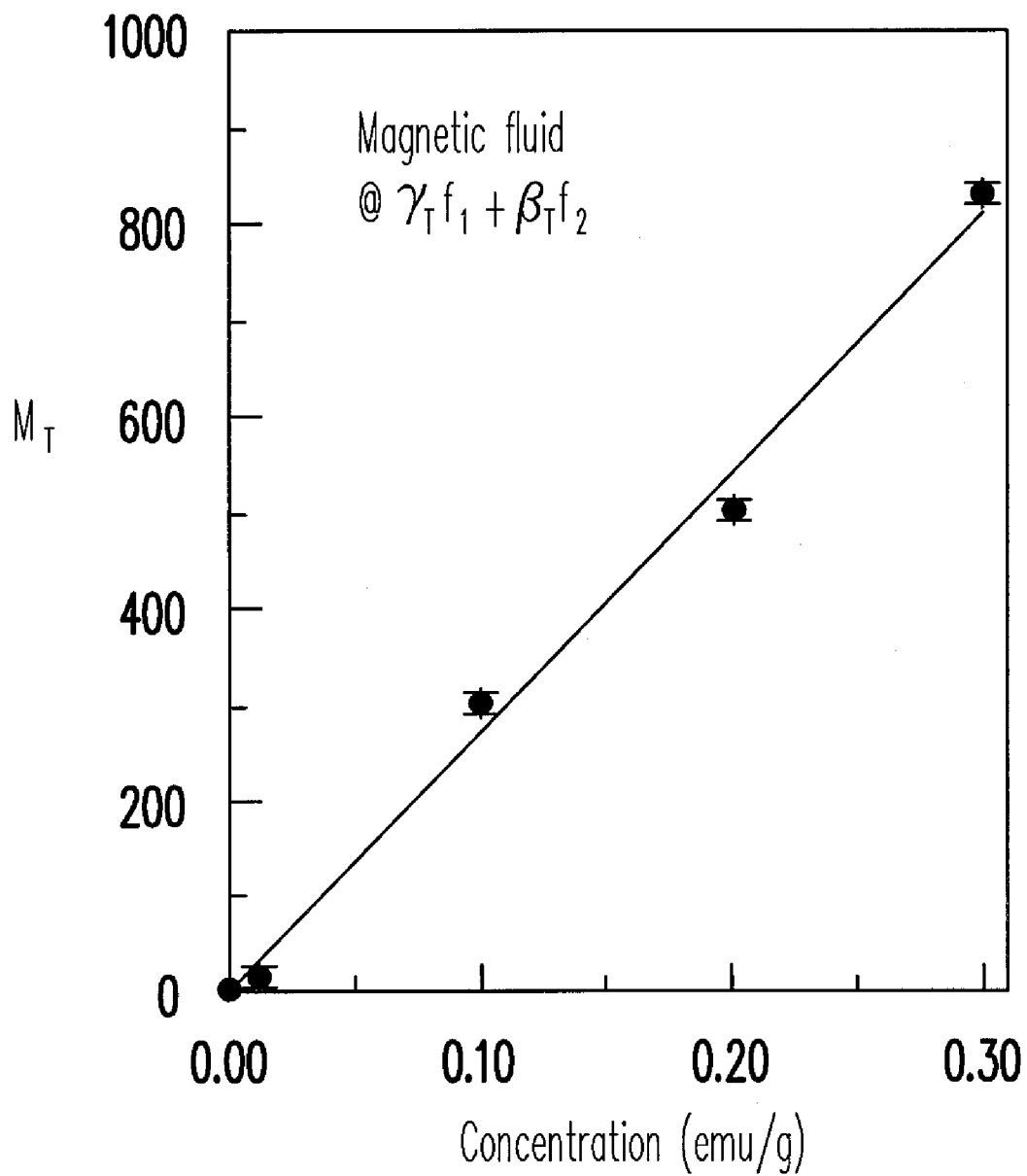
FIG. 5 schematically shows a relationship between magnetization versus concentration in a sample to be measured.

FIG. 5 schematically shows a relationship between magnetization versus concentration in a sample to be measured. The magnetic fluids in various concentrations from zero to 0.3 emu/g, are measured by the apparatus in FIG. 3. It is noted that the highest concentration of magnetic fluid under detection is not limited to 0.3 emu/g. The higher the concentration is, the more the individual magnetic nanoparticles exist in magnetic fluid. It is expected that the magnetization $M_T$ of the target component at $\gamma_T f_1 + \beta_T f_2$ increases as the concentration of magnetic fluid increases in a linear relation.

The apparatus in FIG. 3 with the circuit architecture in FIG. 4 can have various applications, such as assay on bio-molecules via immunomagnetic reduction. As evidenced with the results in FIG. 5, the $M_T$ become less as the concentration of magnetic fluid, i.e. the number of individual magnetic nanoparticles in liquid, is reduced. The apparatus of the present invention can precisely measure the magnetization of the magnetic fluid and observe the variation. By utilizing this property, a method to detect bio-molecules in liquid is developed. In such method, bio-probes like anti-bodies are coated onto magnetic nanoparticles.

Figure 6:
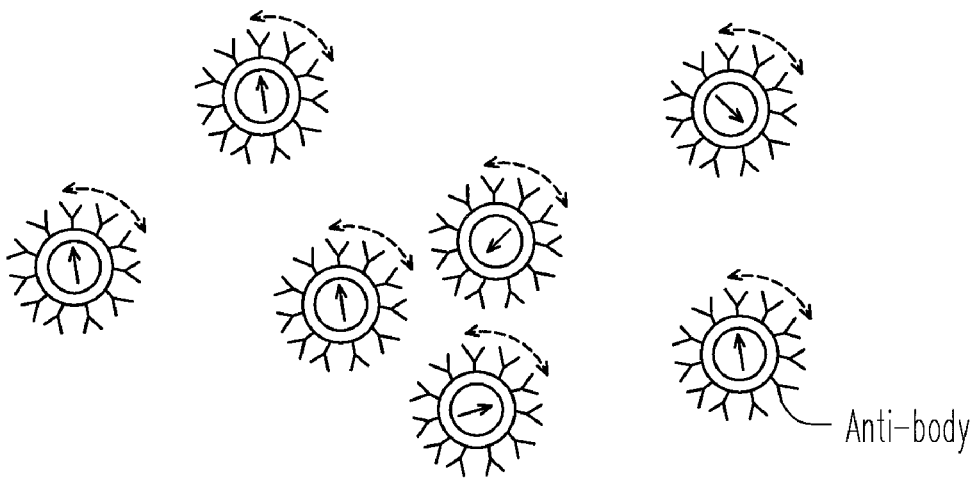
FIG. 6 schematically shows a reaction mechanism between the magnetic nanoparticles coated with bio-probe and the bio-molecule to be measured, according to an embodiment of the present invention.
Figure 6:
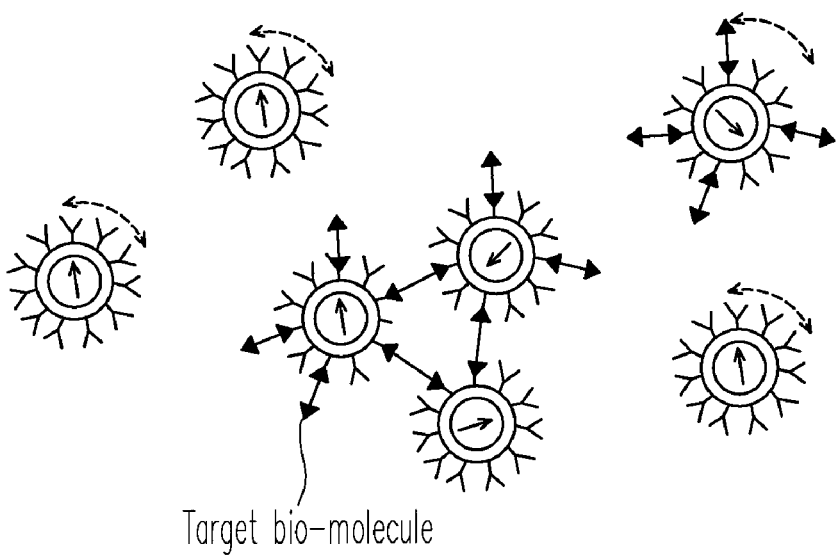

FIG. 6 schematically shows a reaction mechanism between the magnetic nanoparticles coated with bio-probe and the bio-molecule to be measured, according to an embodiment of the present invention. Thus, the magnetic nanoparticles are specifically bio-functionalized and are able to associate with target bio-molecules. Due to the association, portion of individual bio-functionalized magnetic nanoparticles become physically larger or clustered. In FIG. 6(a), when the magnetic nanoparticles with the coated anti-body do not react with the bio-molecule to be detected, the magnetization is the initial state at $M_{T,o}$. The magnetic nanoparticles are small and the rotation is easier. In FIG. 6(b), however, if the nanoparticles have reacted with the target bio-molecule, some magnetic nanoparticles are becoming larger or joined together in a cluster. In this situation, the magnetization $M_{T,\phi}$ of the sample is supposed to be less than that of the initial state $M_{T,o}$, when bio-functionalized magnetic nanoparticles bind with target bio-molecules in magnetic fluid. This is the mechanism to perform assay method as ImmunoMganetic Reduction (IMR).

Figure 7:
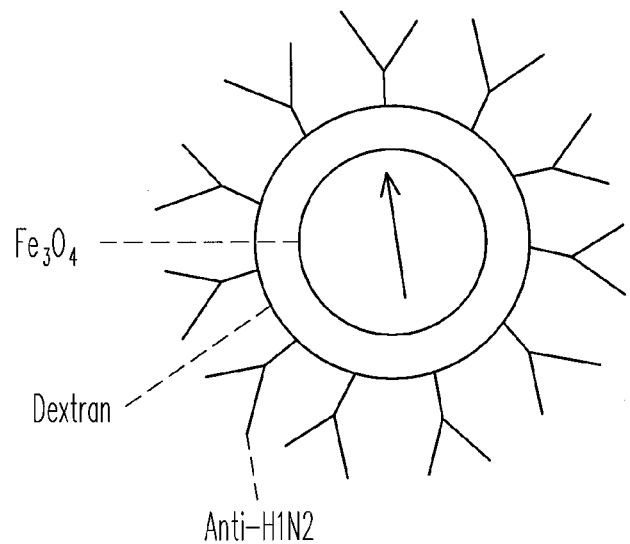
FIG. 7 schematically shows a structure of magnetic nanoparticles coated with bio-probe, according to an embodiment of the present invention.
Figure 8:
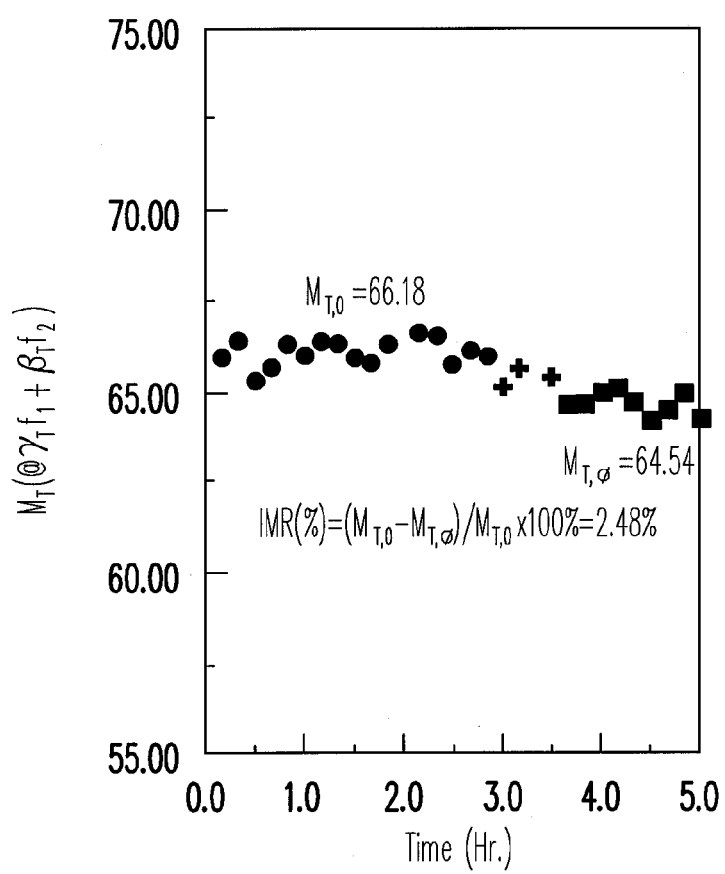
FIG. 8 schematically shows a reaction expressed by the magnetization as a function of a time, according to an embodiment of the present invention.

An example to show the reduction in $M_T$ caused by the association between bio-functionalized magnetic nanoparticles and target bio-molecules is given. FIG. 7 schematically shows a structure of magnetic nanoparticles coated with bio-probe, according to an embodiment of the present invention. In FIG. 7, for a single magnetic nanoparticle, it can be $Fe_3O_4$, for example. The magnetic nanoparticle is coated with dextran and then bio-probe (or antibody), such as polyclonal anti-H1N2 is used in this example. In addition to polyclonal antibodies, monoclonal antibodies can also be used for bio-probe. The H1N2 is one of swine-influenza viruses as the bio-molecule to be detected in amount. To detect the target bio-molecule H1N2, 40-μl magnetic reagent of 0.02 emu/g in concentration (i.e. magnetic fluid having anti-H1N2 bio-functionalizing magnetic nanoparticles) is mixed with 60-μl H1N2 solution, in which the concentration is 0.032 HAU/50-μl in this example. After mixing, the time-dependence $M_T$ of the mixture of magnetic reagent and H1N2 solution is detected by using the apparatus schematically shown in FIGS. 3 and 4. FIG. 8 shows a reaction expressed by the magnetization as a function of a time, according to an embodiment of the present invention. In FIG. 8, the round dots denote the $M_T$ of the mixture of magnetic reagent and H1N2 solution before incubation. The dots distributed at a stable state in time. The $M_T$ before incubation is denoted with $M_{T,o}$. The time-average value is taken for the collected data 2 hours for example. The $M_{T,o}$ is measured as 66.18 under the target mixed frequency of $\gamma_T f_1 + \beta_T f_2$. The cross dots correspond to the processes that the bio-functionalized magnetic nanoparticles are binding with target bio-molecules H1N2. After the binding/incubation at room temperature, such as 22° C. The $M_{T,\phi}$ represents the averaged $M_T$ for the data after the mixture of magnetic reagent and H1N2 solution has been incubated and reached to another stable state, as shown with square dots. The cross dots represent the transition state. As described in FIG. 6, the magnetization $M_{T,\phi}$ becomes smaller after a sufficient incubation time. It must be noted the incubation time generally depends on the quality of bio-probe and the incubation temperature. The incubation temperature can be, for example, from 18° C. to 45° C. and the incubation time can be, for example, 1 minute to 5 hours. If the incubation temperature is increased, the incubation time is expected to be reduced. The time-average value of the square dots is around 64.54 for $M_{T,\phi}$. The significant reduction in $M_T$ evidences the conjugation between bio-functionalized magnetic nanoparticles and bio-molecules H1N2. Moreover, the IMR signal can be obtained as 2.48% via $$IMR(\%) = (M_{T,o} - M_{T,\phi})/M_{T,o} \times 100\%. \quad (7)$$

For several tests, the mean value and the standard deviation are 2.48% and 0.09%, respectively. The result approves the presumption made in the present invention.

Figure 9:
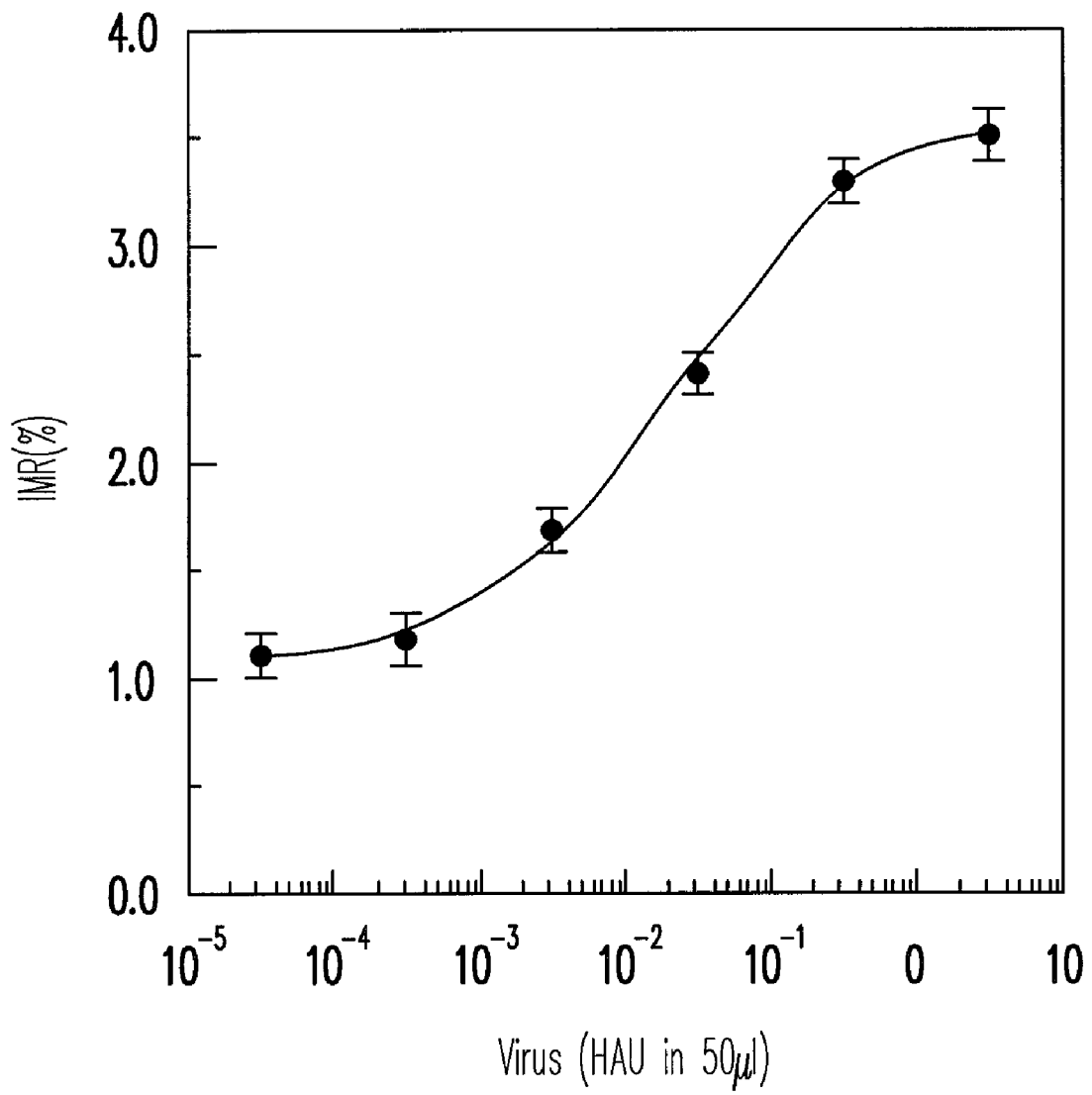
FIG. 9 schematically shows a behavior of IMR (%) versus a virus concentration, according to an embodiment of the present invention.

In further studies, various concentrations of bio-molecule have been measured in IMR (%). FIG. 9 shows a behavior of IMR (%) versus a virus concentration, according to an embodiment of the present invention. In FIG. 9, the relationship between IMR and the concentration of target bio-molecules, such as virus of H1N2 in this example, is investigated. At concentrations lower than $3 \times 10^{-4}$ HAU/50-μl, IMR signals are near the noise level of the detecting device. As the concentration of H1N2 is higher than $3 \times 10^{-4}$ HAU/50-μl, IMR signal increases exponentially with the increasing concentration of H1N2, and then almost reaches to a saturated value at high concentrations. It is found in the present invention that the relationship between IMR and the concentration $\phi$ of target bio-molecules H1N2 in FIG. 9 behaves following Sigmoid function as the equation (8):

$$IMR(\%) = \frac{A-B}{1+\left(\frac{\phi}{\phi_o}\right)^\rho} + B, \quad (8)$$

where the parameter A in Eq. (8) corresponds to the noise level of this assay and B denotes the saturated IMR signal at high concentrated target bio-molecules. Through fitting the data points in FIG. 9 to Eq. (8), A, B, $\phi_o$, and $\rho$ can be found as 1.06, 3.65, 0.024, and 0.64, respectively. The correlation coefficient $R^2$ is 0.997 for that in FIG. 9. So, the measured quantity of IMR as a function of concentration $\phi$ of bio-molecule to be detected is very high and is well defined by Eq. (8).

The logistic behavior expressed with Eq. (8) for the IMR-$\phi_o$ curve is found not only H1N2, but also for other kinds of bio-molecules. The bio-molecules can include, for example, proteins, viruses, nuclei acids, and even chemicals. Of course, the parameters A, B, $\phi_o$, and $\rho$ may vary for different kinds of target bio-molecules. However, according to the investigation of the present invention, an universal curve for IMR-$\phi_o$ relationships of different bio-molecules or chemicals by scaling IMR to (IMR−A)/(B−A), and $\phi$ to $\phi/\phi_o$ can describe various samples in the same curve in Eq. (8), which is further expressed into Eq. (9):

$$IMR_{nor} = (IMR-A)/(B-A) = 1 - \frac{1}{1-\Phi^\rho}, \Phi = \phi/\phi_o. \quad (9)$$

Figure 10:
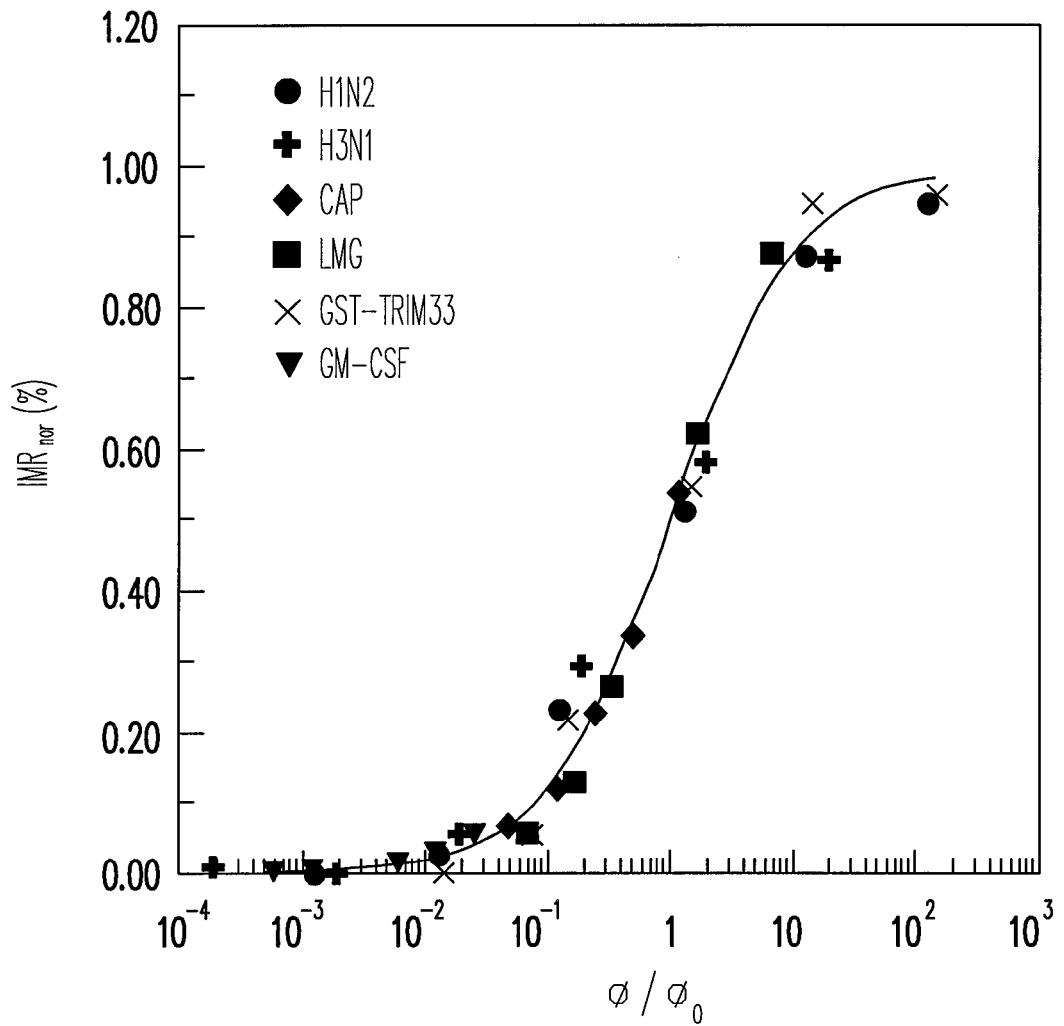
FIG. 10 schematically shows a behavior of $IMR_{nor}$ (%) in normalization versus a concentration of bio-molecule, according to an embodiment of the present invention.

In Eq. (9), the normalized IMR, denoted as $IMR_{nor}$ is a function of the normalized concentration $\Phi$ without parameters of A, B and $\phi_o$. The only parameter to be fitted is $\rho$ in a general form. FIG. 10 schematically shows a behavior of $IMR_{nor}$ in normalization versus a normalized concentration of bio-molecules, according to an embodiment of the present invention. In FIG. 10, several samples are measured to produce the curve like that in FIG. 9. The results show that the universal curve for assaying various bio-molecules. $IMR_{nor}$ (%) titled in the y axis in FIG. 10 is (IMR−A)/(B−A) in unit of percents. The parameters A, B, $\phi_o$, and $\rho$ for the assays on various bio-molecules shown in FIG. 10 are tabulated in Table 1.

TABLE 1

| Bio-molecule | Antibody type | Parameter | | | |
| --- | --- | --- | --- | --- | --- |
| | | A | B | $\phi_o$ | $\rho$ |
| H1N2 | Polyclonal | 1.06 | 3.65 | 0.024 | 0.64 |
| H3N1 | Polyclonal | 0.96 | 5.34 | 0.060 | 0.50 |
| Chloramphenicol (CAP) | Monoclonal | 0.65 | 6.26 | 2.24 | 0.94 |
| Leuco-malachite green (LMG) | Monoclonal | 0.75 | 8.86 | 1.78 | 1.01 |
| GST-TRIM33 | Polyclonal | 0.63 | 3.23 | 69.46 | 0.86 |
| GM-CSF | Monoclonal | 0.81 | 14.53 | 0.819 | 0.77 |

In other words, Eq. (9) can be the general curve to describe various bio-molecules. In the practical applications, one can measure the IMR for a sample with respect to a specific bio-molecule by the apparatus as, for example, shown in FIGS. 3 and 4. Then, the concentration $\phi$ of the bio-molecule to-be-detected can be obtained, according to Eq. (8) or Eq. (9) and a prepared table. The bio-probe provider may prepare the parameter table based on Eq. (8) or Eq. (9), so that the user can simply measure the concentration of the bio-molecule by measuring the quantities IMR. The measuring apparatus can be, for example, the apparatus in FIG. 3 and FIG. 4 with solenoids to produce ac magnetic field at the mixed frequency. However, the quantities IMR may be measured by other manner without limited to the solenoid-base. The apparatus in FIG. 3 and FIG. 4 is not the only choice in the present invention to measure the IMR.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. An apparatus to measure ac magnetization at mixture frequency, comprising:
    an ac generating unit to generate at least a first ac current with a frequency $f_1$ and a second ac current with a frequency $f_2$;
    a co-axial solenoid unit, driven by the first ac current and the second ac current to generate a first magnetic field and a second magnetic field;
    a pick-up solenoid, within the co-axial solenoid unit, wherein a sample is disposed in the pick-up solenoid for detecting an ac magnetization of the sample and multiple frequency-component signals corresponding to various frequency combinations of $f_1$ and $f_2$ are output; and
    a signal processing circuit, receiving the frequency-component signals, wherein the signal processing circuit processes the frequency-component signals and obtains the ac magnetization of the sample at a target frequency of $(\gamma_T f_1 + \beta_T f_2)$, wherein $\gamma_T$ and $\beta_T$ are positive integers and the frequency $f_1$ and the frequency $f_2$ are two different frequencies.

2. The apparatus according to claim 1, wherein the frequency $f_1$ and the frequency $f_2$ are in a range from $10^1$ to $10^6$ Hz.

3. The apparatus according to claim 1, wherein the pick-up solenoid includes magnetometer or gradiometer-type.

4. The apparatus according to claim 1, wherein the pick-up solenoid is also co-axial to the co-axial solenoid unit.

5. The apparatus according to claim 1, wherein the signal processing circuit comprises:
    a digital signal processor;
    n stages of amplifiers and filters connected in series, where n is at least 2, a first amplifier is connected to the pick-up solenoid for receiving the frequency-component signals, and the filters are filtering out a component with the target frequency;
    a plurality of analog to digital converters, respectively coupled between the filters and the digital signal processor to convert output signals of the filters into digital quantities for the digital signal processor; and
    a plurality of digital to analog converters, respectively coupled from the digital signal processor to the amplifiers, wherein the digital signal processor produces a suppressing signal and the suppressing signal is fed back to the connected amplifiers to suppress a portion of the output signal from a previous-stage one of the filters other than the target frequency.

6. The apparatus according to claim 5, wherein a central frequency of the filters is located at the target frequency in a mixed frequency.

7. The device according to claim 5, wherein the suppressing signal produced from the digital signal processor is to cancel signals at harmonic frequencies generated by the co-axial solenoid unit and sub-harmonic frequencies induced by electronic circuit.

* * * * *